United States Patent
Laroche et al.

(10) Patent No.: US 9,169,222 B2
(45) Date of Patent: Oct. 27, 2015

(54) PROCESS FOR MAKING ALKOXYLATED PIPERAZINE COMPOUNDS

(75) Inventors: Christophe R. Laroche, Lake Jackson, TX (US); Daniel A. Aguilar, Lake Jackson, TX (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 14/238,338

(22) PCT Filed: Aug. 24, 2012

(86) PCT No.: PCT/US2012/052179
§ 371 (c)(1),
(2), (4) Date: Feb. 11, 2014

(87) PCT Pub. No.: WO2013/032874
PCT Pub. Date: Mar. 7, 2013

(65) Prior Publication Data
US 2014/0256944 A1    Sep. 11, 2014

Related U.S. Application Data

(60) Provisional application No. 61/527,822, filed on Aug. 26, 2011.

(51) Int. Cl.
*C07D 295/088* (2006.01)
*C07D 241/04* (2006.01)

(52) U.S. Cl.
CPC .......... *C07D 295/088* (2013.01); *C07D 241/04* (2013.01)

(58) Field of Classification Search
CPC .................................................... C07D 295/088
USPC .......................................................... 544/401
See application file for complete search history.

(56) References Cited

U.S. PATENT DOCUMENTS

| 5,334,763 A | 8/1994 | Washington et al. |
| 5,395,973 A | 3/1995 | Washington et al. |

FOREIGN PATENT DOCUMENTS

GB        2333774 A    *   8/1999    ........... C07D 241/08

* cited by examiner

*Primary Examiner* — Kristin Vajda

(57) ABSTRACT

The present invention relates to an improved process for making mono- and di-alkoxylated piperazine compounds especially dihydroxyethylpiperazine. The improvement comprises the addition of an acid to the piperazine compound prior to the addition of an alkylene oxide to a reactor wherein the alkoxylated piperazine compound is prepared. Said improvement reduces the concentration of undesirable glycol ether byproducts which contribute undesirable color and foaming of the alkoxylated piperazine compounds.

9 Claims, No Drawings

PROCESS FOR MAKING ALKOXYLATED PIPERAZINE COMPOUNDS

FIELD OF THE INVENTION

The present invention relates to an improved process for making mono- and di-alkoxylated piperazine compounds especially dihydroxyethylpiperazine. Said improvement reduces the concentration of undesirable glycol ether byproducts which contribute to color formation and foaming of the alkoxylated piperazine compounds.

BACKGROUND OF THE INVENTION

The present invention relates to the manufacture of mono- and/or di-alkoxylated piperazine compounds from alkylene oxides and a piperazine compound. Common byproducts of these alkoxylated piperazine compounds include glycol ether byproducts. The undesirability of glycol ether byproducts in known, for example see U.S. Pat. Nos. 5,334,763 and 5,395,973 which discloses the reduction of ethoxylated or glycol ether amine byproducts in the production of mono-, di-, and triethanolamines by adding carbon dioxide. These byproducts contribute to unwanted color and/or the generation of foam during use, for example in such applications as hard surface cleaning, corrosion inhibition, and the like. Because such byproducts are also undesirable in certain commercial uses of mono- and/or di-alkoxylated piperazine compounds, it would be desirable to have a process to make mono- and/or di-alkoxylated piperazine compounds having better (e.g., less) color and lower tendency to foam.

SUMMARY OF THE INVENTION

The present invention is an improvement in a process and under conditions for making an alkoxylated piperazine compound from the reaction of an alkylene oxide and a piperazine compound wherein undesirable glycol ether byproducts are formed, the improvement which comprises the addition of an acid to a reaction mixture comprising a piperazine compound, preferably an aqueous solution comprising from 1 to 70 percent of a piperazine compound prior to the addition of an alkylene oxide to a reactor wherein the alkoxylated piperazine compound is prepared.

Preferably in the improved process as defined herein above the acid is present in an amount of from 0.001 to 5 weight percent based on the total weight of the aqueous solution.

Preferably in the improved process as defined herein above the acid is a mineral acid or an organic acid having a pKa of equal to or less than 13.

Preferably in the improved process as defined herein above the acid is phosphoric acid, sulfuric acid, hydrochloric acid, boric acid, nitric acid, a carboxylic acid, phenol, phenol derivative, or an alcohol.

Preferably in the improved process as defined herein above the alkylene oxide is ethylene oxide, propylene oxide, butylene oxide, or epichlorohydrin.

Preferably in the improved process as defined herein above the alkylene oxide is present in an amount of from 0.5 to 2.5 mol equivalents of an alkylene oxide for each NH based on the amount of piperazine compound.

Preferably in the improved process as defined herein above the process is conducted at a reaction temperature of less than 250° C.

Preferably in the improved process as defined herein above the acid is added to the reactor in a process for making dihydroxyethylpiperazine compound.

DETAILED DESCRIPTION OF THE INVENTION

The present invention is based on the discovery that, in processes and under conditions for making mono- and/or di-alkoxylated piperazine compounds wherein glycol ethers are formed as undesired byproducts, the levels of at least these undesirable byproducts are reduced or such byproducts substantially eliminated by the addition of even very small amounts of an acid to a reactor wherein such mono- and/or di-alkoxylated piperazine compounds are prepared.

In the present invention, the piperazine compound can be represented by the formula:

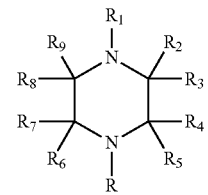

wherein R, $R^1$, $R^2$, $R^3$, $R^4$, $R^5$ $R^6$, $R^7$, $R^8$, and $R^9$ are each independently hydrogen, an alkyl group, aryl group, $-(CH_2-CH_2-O)_n-H$ wherein n is an integer from 0 to 8, an hydroxyalkyl group, an aminoalkyl group where the nitrogen can be part of a 5 or 6 ring membered cycle, an alkylene group containing quaternary ammonium, a carboxylic acid and/or a salt thereof, or a sulphonic acid and/or a salt thereof, preferably $R_1$, $R_2$, $R_3$, and $R_4$ are all hydrogen, with the proviso that at least one of R and $R^1$ is a hydrogen.

Suitable alkylene oxides are substituted oxiranes and are represented by the formula:

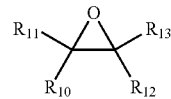

wherein $R_{10}$, $R_{11}$ $R_{12}$, and $R_{13}$ are independently hydrogen, halogen, alkyl, halogenated alkyl, phenyl, halogenated phenyl, aryl, alkaryl, an alkylene-linked aromatic ether moiety, or heterocyclic polyvalent group. Preferred alkylene oxides are ethylene oxide, propylene oxide, butylene oxide, epichlorohydrin, styrene oxide, or phenylglycidyl ether.

In connection with the aforementioned discovery, it has been determined with respect to the production of alkoxylated piperazine compounds (from an alkylene oxide and piperazine compound) that the alkoxylated piperazine byproducts are formed through a quaternary piperazine alkoxide ion pair intermediate, we believed, according to a mechanism to be described below for the reaction of piperazine with ethylene oxide. Corresponding quaternary piperazine alkoxide ion pairs are believed to be formed (or are capable of being formed under certain reaction temperatures and conditions) in the manufacture of other alkoxylated piperazine compounds wherein an alkylene oxide other than ethylene oxide, such as propylene oxide, butylenes oxide, is used.

A most preferred application is for the production of dihydroxyethylpiperazine, and hereafter, it is in the context of this most preferred application that the present invention is described and illustrated although those skilled in the art will be well able to adapt the invention to processes for other alkoxylated piperazine compounds. The quaternary piperazine precursor for the ethoxylated piperazine byproducts in the production of dihydroxyethylpiperazine is stable for reaction temperatures not exceeding about 150° C., and it is in processes conducted at such temperatures that the present invention is most useful. The quaternary ammonium precursor is less stable, and therefore less of a problem in terms of ethoxylated piperazine formation, for processes involving reaction temperatures of from about 150° C. up to about 250° C.

The primary advantage of the present invention, however, is that it permits the reaction of ethylene oxide and the piperazine compound to proceed with a significant reduction in the levels of the glycol ethers as byproducts or their substantial elimination.

It is believed that the quaternary piperazine precursor is formed substantially as follows:

Scheme 1:

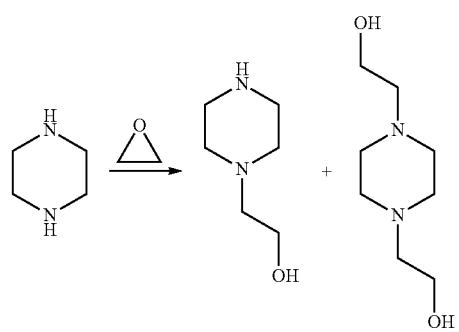

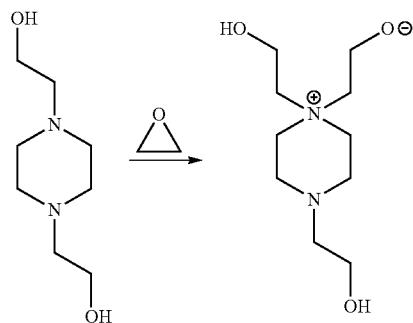

The reaction of quaternary piperazine ion pair with ethylene oxide leads to the formation of various glycol ether alkoxides. In the absence of an acid, quaternary piperazine precursors may form one or more glycol ether byproducts (collectively referred to as heavies), including ethylene glycol as follows. The reactions in scheme 2 are not intended to be inclusive of every, or all, possible glycol ether byproduct generating reactions.

Scheme 2:

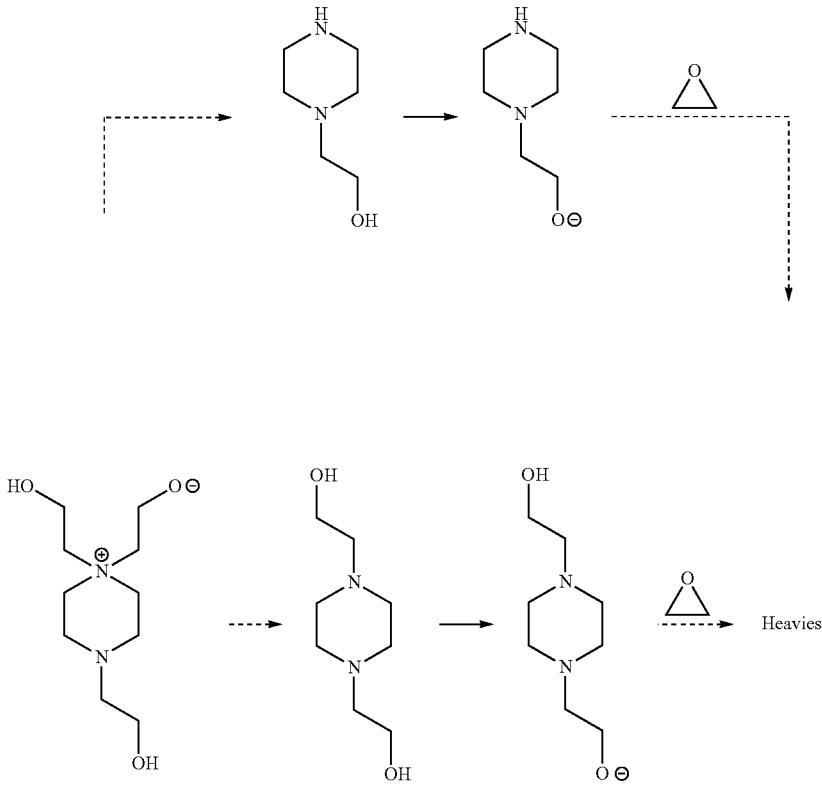

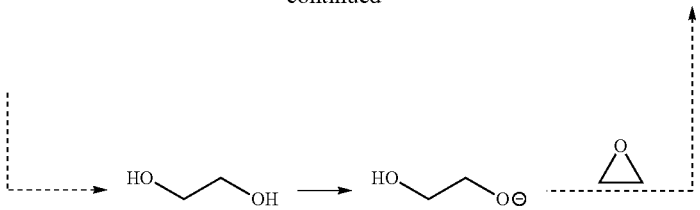

It has been shown that over alkoxylation of piperazine compounds leads to foaming. Our work has determined that heavies resulting from alkoxylates also contribute significantly to foaming, the higher the concentration of alkoxylates, the more foaming. Foaming causes a variety of process and end use problems, such as reduction of pump efficiency (i.e., cavitations), reduced capacity of pumps and storage tanks, bacterial growth, dirt flotation, dirt deposit formation, reduced effectiveness of the fluid solution, downtime to clean tanks, drainage problems in sieves and filters, cost of material rejection due to imperfections, and the like. The process improvement of the present invention reduces and/or eliminates foaming of the alkoxylated piperazine compound due to the formations of alkoxylates.

In the process of the present invention, the alkoxylation of the piperazine compound may be accomplished under anhydrous conditions by melting the piperazine compound, e.g., the reaction mixture is the piperazine compound neat. Preferably, alkoxylation of the piperazine compound is accomplished by preparing a reaction mixture comprising 1 to 70 weight percent aqueous solution of piperazine compound in water, from 0.001 to 5 weight percent of an acid based on the total weight of the reaction mixture, and from 0.5 to 2.5 mol equivalents per NH of an alkylene oxide based on the amount of the piperazine compound. Preferably the acid is added to the piperazine compound prior to the addition of the alkylene oxide.

The reaction temperature is dependent on the alkylene oxide used. Preferably, the reaction temperature is equal to or less than 250° C., preferably equal to or less than 200° C., more preferably equal to or less than 170° C., more preferably equal to or less than 150° C. Preferably, the reaction temperature is equal to or greater than 40° C., preferably equal to or less than 80° C., more preferably equal to or less than 100° C., more preferably equal to or less than 120° C.

The alkoxylation reaction is allowed to proceed until the desired level of piperazine compound is converted to dihydroxyalkylpiperazine compound, preferably equal to or greater than 50 percent conversion, more preferably equal to or greater than 60 percent conversion, more preferably equal to or greater than 70 percent conversion, more preferably equal to or greater than 80 percent conversion, more preferably equal to or greater than 90 percent conversion, and most preferably equal to or greater than 95 percent conversion of the piperazine compound to dihydroxyalkylpiperazine compound.

If the reaction mixture is an aqueous solution, preferably the piperazine compound is present in an amount of equal to or less than 70 weight percent based on the total weight of the reaction mixture, preferably equal to or less than 60 weight percent, more preferably equal to or less than 50 weight percent based on the total weight of the reaction mixture. If the reaction mixture is an aqueous solution, preferably the piperazine compound is present in an amount of equal to or greater than 1 weight percent based on the total weight of the reaction mixture, preferably equal to or greater than 10 weight percent, more preferably equal to or greater than 20 weight percent based on the total weight of the reaction mixture.

Alkoxides have a pKa value of 13 to 15. Piperazine and hydroxyethylpiperazine have pKa values of 9.7 and 9.1, respectively. We have found that the addition of a proton donor compound, referred to herein after as an acid, such as an organic acid or mineral acid mitigates the formation of glycol ether byproducts by protonating the alkoxides which are orders of magnitude more basic than piperazine and hydroxyethylpiperazine. Preferred acids are proton donor compounds having a pKa equal to or less than 13, more preferably a pKa equal to or less than 11, more preferably a pKa equal to or less than 9, and more preferably a pKa equal to or less than 5. Examples of suitable mineral acids are phosphoric acid, sulfuric acid, hydrochloric acid, boric acid, nitric acid, and the like. Examples of suitable organic acids are carboxylic acids, phenol, phenol derivatives, alcohols, and the like.

Preferably the acid is added to the reaction mixture in an amount of equal to or less than 5 weight percent based on the total weight of the reaction mixture, preferably equal to or less than 2.5 weight percent, more preferably equal to or less than 2 weight percent, even more preferably equal to or less than 1.5 weight percent, and even more preferably equal to or less than 1 weight percent based on the total weight of the reaction mixture. Preferably the acid is added to the reaction mixture in an amount of equal to or greater than 0.001 weight percent based on the total weight of the reaction mixture, preferably equal to or greater than 0.01 weight percent, and more preferably equal to or greater than 0.1 weight percent based on the total weight of the reaction mixture.

Preferably the alkylene oxide is added to the reaction mixture in an amount of equal to or less than 3 mol equivalents for each NH based on the amount of piperazine compound, preferably equal to or less than 2.5 mol equivalents, more preferably equal to or less than 2 mol equivalents for each NH based on the amount of piperazine compound. Preferably the alkylene oxide is added to the reaction mixture in an amount of equal to or greater than 0.5 mol equivalents for each NH, preferably equal to or greater than 1 mol equivalents, preferably equal to or greater than 1.5 mol equivalents for each NH based on the amount of piperazine compound.

EXAMPLES

The Examples and Comparative Example are run at 120° C. in a heated stainless steel 9 liter (L) stirred reactor. In Example 1 and 2 and Comparative Example A, 3 kilograms (kg) of a 33 percent by weight solution of piperazine in water is charged to the reactor. Ethylene oxide (EO) is metered into the reactor over several hours at 120° C. using a molar ratio of 1.9:1.0 (EO:piperazine). In Example 1, 0.5 weight percent sulfuric acid (98% $H_2SO_4$) is added before the addition of the ethylene oxide. In Example 2, 5 weight percent monobasic sodium phosphate (NaH$_2$PO$_4$) is added before the addition of the ethylene oxide. Subsequent to the completion of ethylene oxide addition, the reaction is allowed to agitate for several hours at reaction temperature to consume residual ethylene oxide. The resulting reaction mixtures are tested as produced.

Foam is determined as follows: a 100 milliliter (ml) sample (e.g., the reacted mixture of Examples X to Y and Comparative Examples Z to W) is added to a 500 ml graduated cylinder containing a bubble diffuser connected to a dry air supply. The reaction mixture and diffuser, without air passing through it, are allowed to equilibrate for 2 minutes. The combined height (i.e., 100 ml plus the volume displaced by the diffuser) is measured and recorded in milliliters. After the 2 minute equilibration time, air is passed through the solution for one minute at a rate of 1000 ml/min then stopped. The resulting final foam volume is immediately measured in milliliters. The final volume minus the starting volume is reported as Foam Height (ml). The time for the foam to collapse until the first appearance of liquid is measured and reported as Break Time (seconds (s)). The results are listed in Table 1.

The amount of glycol ether byproducts (combination of trimeric and tetrameric ethoxylated piperazine compounds) are analyzed by gas chromatography using an Agilent Technologies Model 7890 GC equipped with a J&W Scientific DB-WAX column. Identification of the compounds has been performed using Mass spectroscopy in positive chemical ionization mode and the amounts in weight percent are shown in Table 1. As used herein, trimeric piperazine compound is defined as the reaction product(s) of piperazine with three ethylene oxide and tetrameric piperazine compound is defined as the reaction product(s) of piperazine with four ethylene oxide.

Color is determined according to ASTM 1544 using a Lovibond PFX195 tintometer with a path of 10.0 mm

TABLE 1

| Example Comparative Example | A | 1 | 2 |
|---|---|---|---|
| Acid | none | 98% H$_2$SO$_4$ | NaH$_2$PO$_4$ |
| Foam Height, ml | 155 | 20 | 30 |
| Break Time, s | 34 | 4 | 7 |
| Trimeric + Tetrameric, wt % | 1.13 | 0.64 | 0.51 |
| Color, GCU | 4 | 0.7 | 0.5 |

The invention claimed is:

1. A process for decreasing the production of undesirable glycol ether byproducts in the alkoxylation of a piperazine compound by reaction with an alkylene oxide, wherein the piperazine compound has the formula:

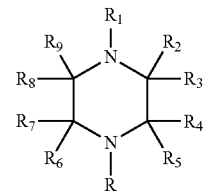

wherein R, R$^1$, R$^2$, R$^3$, R$^4$, R$^5$ R$^6$, R$^7$, R$^8$, and R$^9$ are each independently hydrogen, an alkyl group, aryl group, —(CH$_2$—CH$_2$—O)$_n$—H wherein n is an integer from 0 to 8, an hydroxyalkyl group, an aminoalkyl group where the nitrogen can be part of a 5 or 6 ring membered cycle, an alkylene group containing quaternary ammonium, a carboxylic acid and/or a salt thereof, or a sulphonic acid and/or a salt thereof, with the proviso that at least one of R and R$^1$ is a hydrogen;

which process comprises adding an acid to a reaction mixture comprising the piperazine compound prior to the addition of the alkylene oxide to a reactor wherein the alkoxylated piperazine compound is prepared.

2. A process according to claim 1 wherein the reaction mixture is a 1 to 70 weight percent aqueous solution of the piperazine compound.

3. A process according to claim 1 wherein the acid is present in an amount of from 0.001 to 5 weight percent based on the total weight of the reaction mixture.

4. A process according to claim 1 wherein the acid is a mineral acid or an organic acid having a pKa of equal to or less than 13.

5. A process according to claim 1 wherein the acid is phosphoric acid, sulfuric acid, hydrochloric acid, boric acid, nitric acid, a carboxylic acid, phenol, phenol derivative, or an alcohol.

6. A process according to claim 1 wherein the alkylene oxide is ethylene oxide, propylene oxide, butylene oxide, or epichlorohydrin.

7. A process according to claim 1 wherein the alkylene oxide is present in an amount of from 0.5 to 2.5 mol equivalents of an alkylene oxide for each NH based on the amount of piperazine compound.

8. A process according to claim 1 wherein the process is conducted at a reaction temperature of less than 250° C.

9. A process according to claim 1 wherein an acid is added to the reactor in a process for making dihydroxyethylpiperazine.

* * * * *